United States Patent
Finbow et al.

[11] Patent Number: 5,746,899
[45] Date of Patent: May 5, 1998

[54] ELECTROCHEMICAL GAS SENSOR

[75] Inventors: John Robert Finbow; Malcolm Robert Bulpitt, both of Hampshire, Great Britain

[73] Assignee: City Technology Limited, Portsmouth, United Kingdom

[21] Appl. No.: 749,176

[22] Filed: Nov. 14, 1996

[30] Foreign Application Priority Data

Dec. 20, 1995 [GB] United Kingdom ............ 9526101

[51] Int. Cl.⁶ .................................................. G01N 27/26
[52] U.S. Cl. ......................... 204/415; 204/426; 204/431; 204/432
[58] Field of Search ............................ 204/415, 431, 204/432, 426

[56] References Cited

U.S. PATENT DOCUMENTS 4,587,003  5/1986  Tantram et al. ............ 204/415
4,820,386  4/1989  LaConti ........................ 204/1 T
5,183,550  2/1993  Mattiessen ................... 204/415

FOREIGN PATENT DOCUMENTS 0 486 179   5/1992  European Pat. Off. .
WO 94/04912  3/1994  WIPO .

*Primary Examiner*—Bruce F. Bell
*Attorney, Agent, or Firm*—Lee, Mann, Smith, McWilliams, Sweeney & Ohlson

[57] ABSTRACT

An electrochemical gas sensor comprises sensing and counter electrodes mounted on the same side of a planar support. An electrolyte is in contact with the sensing and counter electrodes. A capillary controls the access of gas to the sensing electrode. A barrier layer extends over the sensing and counter electrodes, the barrier layer being positioned relative to the capillary and the support being non-electrically conductive and being sufficiently porous such that gas from the capillary is guided transversely and laterally through the support first to reach the sensing electrode and then to reach the counter electrode.

14 Claims, 1 Drawing Sheet

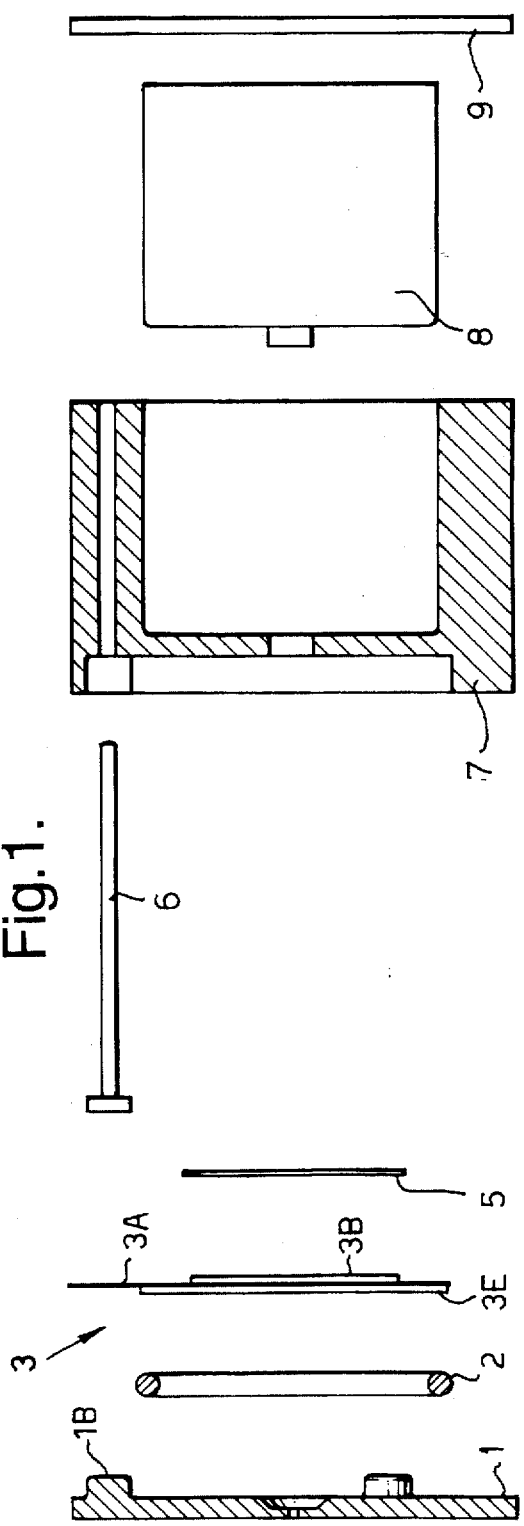
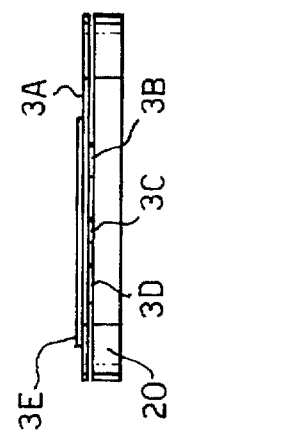
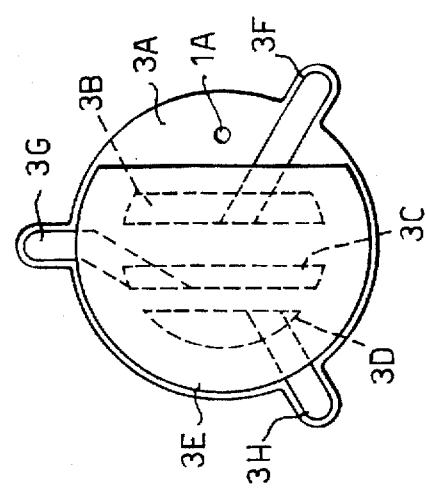
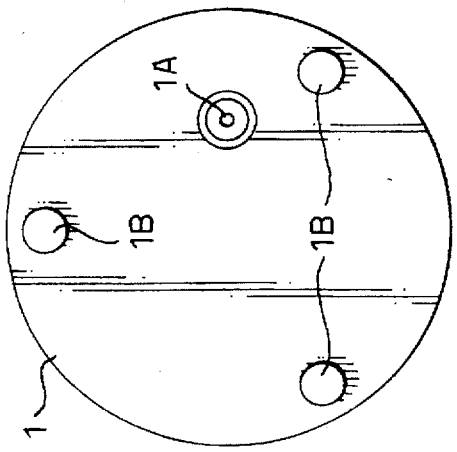

ELECTROCHEMICAL GAS SENSOR

FIELD OF THE INVENTION

The invention relates to an electrochemical gas sensor.

DESCRIPTION OF THE PRIOR ART

Electrochemical gas sensors are well known and are used to detect a variety of gases such as oxygen and toxic gases. A typical electrochemical gas sensor comprises sensing and counter electrodes, an intervening body of electrolyte, and means for controlling the access of gas to the sensing electrode. Examples of known electrochemical gas sensors are described in EP-A-0604012 and U.S. Pat. No. 4,406,770. U.S. Pat. No. 5,298,146 discloses a special type of electrochemical gas sensor which is suitable for detecting more than one gas.

In all these cases, the sensing electrodes have to be spaced significantly from the reference and counter electrodes.

U.S. Pat. No. 4,812,221 discloses a sensor in which the sensing and counter electrodes are arranged in a generally planar manner in contact with an electrolyte. A toxic gas to be detected passes through a porous member to reach the sensing electrode where the toxic gas is removed by electrochemical reaction leaving oxygen free to reach the counter electrode after passing through the electrolyte, which is a relatively slow process.

A more compact sensor is described in U.S. Pat. No. 4,820,386 in which the counter and sensing electrodes are mounted on the same side of a support, laterally spaced apart. However, the oxygen to drive the counter and reference electrode reactions is accessed from the ambient air via channels and thus these electrodes are relatively unprotected from reactant gas in the ambient air.

WO 96/14576 published on 17 May 1996 after the priority date of this present application also discloses a gas sensor with electrodes mounted on a common substrate.

SUMMARY OF THE INVENTION

In accordance with the present invention, an electrochemical gas sensor comprises sensing and counter electrodes mounted on the same side of a planar support; an electrolyte in contact with the sensing and counter electrodes; and means for controlling the access of gas to the sensing electrode and is characterised in that a barrier layer is provided on the support on the opposite side to and extending over the sensing and counter electrodes, the barrier layer being positioned relative to the gas access control means and the support being non-electrically conductive and being sufficiently porous such that gas from the gas access control means is guided transversely and laterally through the support first to reach the sensing electrode and then to reach the counter electrode.

We have devised a new form of electrochemical gas sensor in which the sensing and counter electrodes are mounted on the same, substantially planar support while gas cannot access the counter or sensing electrodes directly. In the new construction, the gas is guided laterally through the support first to the sensing electrode which reacts all the reactant before allowing the gas to be detected (usually oxygen) further to diffuse through the support to the counter electrode. By positively guiding the gas to the sensing electrode, it is ensured that as much as possible of the reactant is removed before the gas proceeds to the counter electrode.

Furthermore, this arrangement allows gas to access the counter electrode without first passing through the electrolyte. This contrasts with conventional sensors in which the electrodes are spaced apart and mounted on separate supports which are subsequently bolted together and results in simpler manufacture.

Typically, the sensor will further comprise a reference electrode and/or an auxiliary electrode mounted on the same side of the support as the sensing and counter electrodes, the arrangement being such that gas can only reach the reference and/or auxiliary electrode after passing the sensing electrode. The use of an auxiliary sensing electrode enables cross-interfering gases and base lines to be cancelled in a conventional manner.

Where a reference and/or auxiliary electrode is provided, the barrier layer is preferably positioned also to force gas to diffuse laterally through the support to reach the reference and/or auxiliary sensing electrode.

The electrolyte can take any conventional form and will typically be an aqueous electrolyte, the support being hydrophobic. In other examples, however, the electrolyte may be a solid electrolyte, the material of the electrolyte being chosen from the group comprising Nafion (perfluorosulfonic acid) (which requires an aqueous supply), polyvinyl alcohol (PVA), poly 2-hydroxy ethyl methacrylate (p-HEMA), polyvinylpyrrolidone (PVP), and polyacrylamide (and substituted polyacrylamides).

The support is conveniently in the form of a backing tape such as porous PTFE. In general, the support will be microporous having a high diffusibility to gas and hydrophobic to prevent electrolyte leakage. Other examples include polypropylene, and fluorinated ethylene propylene.

One of the main advantages of the invention is that the electrodes can be screen printed on the support in a single screen printing operation. This will provide a single component containing all the sensor electrodes which greatly simplifies the sensor assembly.

The control means can be of any conventional form such as a gas phase diffusion barrier, a Knudsen barrier, or a solid membrane.

BRIEF DESCRIPTION OF THE DRAWINGS

Two examples of an electrochemical gas sensor according to the invention will now be described with reference to the accompanying drawings, in which:

FIG. 1 is a schematic, exploded view of a first example;

FIG. 2 is an underneath plan of the top plate in FIG. 1;

FIG. 3 is a plan of the electrode assembly of FIG. 1 but also showing the position of the capillary; and, FIG. 4 is a cross-section through part of a second example.

DETAILED DESCRIPTION OF THE EMBODIMENT

The sensor shown in FIGS. 1–3 comprises a top plate 1 of conventional form having a capillary diffusion barrier 1A and three depending collector pressure pads 1B. The top plate 1 overlies an electrode assembly 3 against which it is compressed in use via an O-ring 2. The electrode assembly 3 (FIG. 3) comprises a disc shaped PTFE backing tape 3A on the under surface of which are screen printed a sensing electrode 3B, a reference electrode 3C, and a counter electrode 3D. It will be noted that the electrodes 3B–3D are laterally spaced apart on the membrane 3A. A solid or impervious polyethylene mask or barrier layer 3E is positioned on the upper surface of the tape 3A in alignment with and covering the sensing, reference and counter electrodes 3B–3D. Each electrode 3B–3D is connected to a respective current collector 3F–3H, the current collectors being aligned with the pressure pads 1B.

It will be noted in FIG. 3 that the capillary hole 1A is positioned off-axis so as to be laterally offset from all the electrodes 3B–3D and the barrier layer 3E.

The electrode assembly 3 is mounted on a plastic electrolyte reservoir body 7 via a separator 5. The top plate 1 is secured to the body 7 by bolting, snap-fitting or ultrasonic welding to secure all the components together. Three pins 6, one of which is shown in FIG. 1 connect to the respective collectors 3F–3H. The body 7 supports a wicking system 8 shown schematically in FIG. 1 which is secured to the body 7 by a closure plate 9. Electrolyte from the body 7 is communicated to the PTFE membrane 3A via the wicking system 8.

In use, gas to be sensed (for example CO in air) diffuses through the capillary 1A and transversely into the membrane 3A due to the presence of the barrier layer 3E. The barrier layer 3E thus prevents the gas being received directly by any of the electrodes 3B–3D. Electrolyte from the reservoir is supplied to the PTFE membrane 3A. The gas then diffuses laterally to the sensing electrode 3B through the membrane 3A and under the barrier layer 3E so that any and all carbon monoxide in the gas will react at the sensing electrode 3B while the non-reacted oxygen to be detected will further diffuse laterally within the PTFE tape 3A underneath the barrier layer 3E so as to reach the reference and counter electrodes 3C and 3D. It will be noted that it is not possible for the incoming gas directly to pass through the PTFE tape 3A to reach the reference and counter electrodes since this would interfere with the operation of the measuring process. The presence and concentration of the gas can be detected by connecting the sensor into a conventional potentiostatic circuit.

It will be noted in FIG. 1 that the electrode assembly 3 is itself a very compact and thin design and a single assembly makes it very much simpler to construct the overall sensor since there are significantly fewer components.

In the example described, the electrolyte is supplied in a conventional form from a reservoir. In other examples, the wicking system 8 could be replaced by a planar, solid electrolyte of one of the materials described above. This would lead to an even more compact design.

FIG. 4 illustrates schematically part of another gas sensor similar to that shown in FIGS. 1 to 3 but in which the wicking system 8 has been replaced by a planar, solid electrolyte such as Nafion 20. The sensing, reference and counter electrodes 3B, 3C, and 3D are provided on the upper surface of the electrolyte 20 and above them is provided the PTFE tape 3A. The barrier layer 3E is provided on the PTFE tape 3A above the electrodes 3B–3D. In this case, the gas will enter through a capillary (not shown) as before and be guided transversely into and laterally through the PTFE tape 3A to reach the sensing electrode 3B. Any gas not consumed at the sensing electrode 3B will laterally diffuse further through the PTFE tape 3A under the barrier layer 3E and into contact with the electrodes 3C and 3D.

In other examples, the electrodes 3B–3D could be fabricated on the undersurface of the PTFE tape 3A which is then assembled with the electrolyte 20.

We claim:

1. An electrochemical gas sensor comprising sensing and counter electrodes mounted on the same side of a planar support; an electrolyte in contact with said sensing and counter electrodes; means for controlling the access of gas to said sensing electrode; and a barrier layer provided on said support on the opposite side to and extending over said sensing and counter electrodes, said barrier layer being positioned relative to said gas access control means and said support being non-electrically conductive and being sufficiently porous such that gas from said gas access control means is guided transversely and laterally through said support first to reach said sensing electrode and then to reach said counter electrode.

2. A sensor according to claim 1, further comprising a reference electrode mounted on the same side of said support as said sensing and counter electrodes, the arrangement being such that gas can only reach said reference electrode after passing said sensing electrode.

3. A sensor according to claim 2, wherein said barrier layer is positioned also to force gas to diffuse laterally through said support to reach said reference electrode.

4. A sensor according to claim 1, further comprising an auxiliary sensing electrode mounted on the same side of said support as said sensing and counter electrodes, the arrangement being such that gas can only reach said auxiliary sensing electrode after passing said sensing electrode.

5. A sensor according to claim 3, wherein said barrier layer is positioned also to force gas to diffuse laterally through said support to reach said auxiliary electrode.

6. A sensor according to claim 1, wherein said barrier layer comprises polyethylene.

7. A sensor according to claim 1, wherein said support comprises porous polytetrafluoroethylene (PTFE).

8. A sensor according to claim 1, wherein said electrodes are screen printed on said support.

9. A sensor according to claim 1, wherein said means for controlling the access of gas to said sensing electrode comprises one of a gas phase diffusion barrier, a Knudsen barrier, and a solid membrane.

10. A sensor according to claim 9, wherein said means for controlling the access of gas to said sensing electrode is a capillary.

11. A sensor according to claim 1, wherein said means for controlling the access of gas to said sensing electrode is laterally offset from said barrier layer.

12. A sensor according to claim 1, wherein said electrolyte is an aqueous electrolyte, and wherein said support is hydrophobic.

13. A sensor according to claim 1, wherein said electrolyte is a solid electrolyte.

14. A sensor according to claim 13, wherein said solid electrolyte is chosen from the group consisting of perfluorosulfonic acid, polyvinyl alcohol (PVA), poly 2-hydroxy ethyl methacrylate (p-HEMA), polyvinylpyrolidone (PVP), and polyacrylamide (and substituted polyacrylamides).

* * * * *